US012655760B2

(12) United States Patent
Kim et al.

(10) Patent No.: US 12,655,760 B2
(45) Date of Patent: Jun. 16, 2026

(54) TUNNEL EXCAVATION APPARATUS TO WHICH SPECTROSCOPIC ANALYSIS METHOD IS APPLIED

(71) Applicant: KOREA RADIOACTIVE WASTE AGENCY, Gyeongju-si Gyeongsangbuk-do (KR)

(72) Inventors: Seung Hyun Kim, Sejong (KR); Hyungoo Kang, Daejeon (KR); Sang Hwan Lee, Daejeon (KR); Sang Hyuk Yun, Daejeon (KR); Yun Jung Choi, Daejeon (KR); Tae Chul Moon, Daejeon (KR)

(73) Assignee: KOREA RADIOACTIVE WASTE AGENCY, Gyeongsangbuk-do (KR)

( * ) Notice: Subject to any disclaimer, the term of this patent is extended or adjusted under 35 U.S.C. 154(b) by 63 days.

(21) Appl. No.: 18/839,366

(22) PCT Filed: Feb. 13, 2023

(86) PCT No.: PCT/KR2023/002068
§ 371 (c)(1),
(2) Date: Aug. 16, 2024

(87) PCT Pub. No.: WO2023/158172
PCT Pub. Date: Aug. 24, 2023

(65) Prior Publication Data
US 2025/0163805 A1     May 22, 2025

(30) Foreign Application Priority Data

Feb. 16, 2022     (KR) ........................ 10-2022-0020066

(51) Int. Cl.
| | |
|---|---|
| *E21D 9/10* | (2006.01) |
| *E21D 9/00* | (2006.01) |

(Continued)

(52) U.S. Cl.
CPC .............. *E21D 9/003* (2013.01); *E21D 9/112* (2013.01); *G01N 21/718* (2013.01); *G01N 33/24* (2013.01)

(58) Field of Classification Search
CPC ....... E21D 9/093; E21D 9/112; G01N 21/718; G01N 33/24
See application file for complete search history.

(56) References Cited

U.S. PATENT DOCUMENTS 5,813,482 A * 9/1998 Barbera .................. E21D 9/108
                                                                175/73
9,840,913 B1 * 12/2017 Levine .................. E21D 11/403
(Continued)

FOREIGN PATENT DOCUMENTS

JP        H09203707 A     8/1997
JP        H11287085 A     10/1999
(Continued)

OTHER PUBLICATIONS

ISA Korean Intellectual Property Office, International Search Report Issued in Application No. PCT/KR2023/002068, May 9, 2023, WIPO, 6 pages.

*Primary Examiner* — Carib A Oquendo
(74) *Attorney, Agent, or Firm* — McCoy Russell LLP

(57) ABSTRACT

The present disclosure relates to a tunnel excavation apparatus to which a spectroscopic analysis method is applied. The tunnel excavation apparatus to which a spectroscopic analysis method is applied may include a ground component measurement unit to measure the properties of the ground which is excavated, and control a first driving unit and a second driving unit to be operated on the basis of the measured information on the ground, thereby preventing cracks from occurring on the ground during a ground excavation process.

5 Claims, 8 Drawing Sheets

(51) Int. Cl.
E21D 9/11 (2006.01)
G01N 21/71 (2006.01)
G01N 33/24 (2006.01)

(56) References Cited

U.S. PATENT DOCUMENTS

| | | | | |
|---|---|---|---|---|
| 2006/0102343 A1* | 5/2006 | Skinner | ................ | B23K 26/082 |
| | | | | 166/57 |
| 2015/0069815 A1* | 3/2015 | Kawai | .................. | E21D 9/1093 |
| | | | | 299/10 |
| 2016/0160641 A1* | 6/2016 | Rowe | .................... | E21B 49/086 |
| | | | | 250/288 |
| 2019/0178036 A1* | 6/2019 | Faircloth | ............. | B23K 26/146 |

FOREIGN PATENT DOCUMENTS

| | | | |
|---|---|---|---|
| JP | 2002296189 A | 10/2002 |
| KR | 20130076907 A | 7/2013 |
| KR | 101542419 B1 | 8/2015 |
| KR | 102431794 B1 | 8/2022 |

* cited by examiner

500

TUNNEL EXCAVATION APPARATUS TO WHICH SPECTROSCOPIC ANALYSIS METHOD IS APPLIED

CROSS REFERENCE TO RELATED APPLICATIONS

The present application is a U.S. National Phase of International Application No. PCT/KR2023/002068 entitled "TUNNEL EXCAVATION APPARATUS TO WHICH SPECTROSCOPIC ANALYSIS METHOD IS APPLIED," and filed on Feb. 13, 2023. International Application No. PCT/KR2023/002068 claims priority to Republic of Korea Patent Application No. 10-2022-0020066 filed on Feb. 16, 2022. The entire contents of each of the above-listed applications are hereby incorporated by reference for all purposes.

TECHNICAL FIELD

The present disclosure relates to a tunnel excavation apparatus to which a spectroscopic analysis method is applied, and more particularly, to a tunnel excavation apparatus to which a spectroscopic analysis method is applied, which measures components of ground to be excavated using a laser induced breakdown spectrometer and has its operation controlled according to the measured components of the ground.

BACKGROUND AND SUMMARY

Tunnel excavation methods are largely divided into conventional tunnel excavation methods and mechanized tunnel excavation methods. The conventional tunnel excavation methods have problems such as high labor costs and long construction periods, and also have problems such as a high incidence of safety accidents.

To solve these problems, the mechanized tunnel excavation methods have been mainly used recently. Among these mechanized tunnel construction methods, mechanized construction using a tunnel boring machine (TBM) is an environmentally friendly tunnel excavation method that is mechanically stable because the cross-section is excavated in a circle, may ensure safety by minimizing ground deformation as it is excavated in a vibration-free and blast-free manner, and can minimize noise and vibration generation.

FIG. 1 is a diagram illustrating a concept of tunnel construction using a tunnel excavation apparatus, FIG. 2 is a perspective view of an excavation unit of the tunnel excavation apparatus, and FIG. 3 is a diagram illustrating a concept of an excavation principle of the tunnel excavation apparatus.

Referring to FIGS. 1 to 3, a plurality of disc cutters 1120 may be mounted on an excavation unit 1100 in front of the tunnel excavation apparatus 1000. Then, when the tunnel excavation apparatus 1000 comes into contact with the ground in front and rotates the excavation unit 1100, rocks or soil in the ground in contact with the excavation unit 1100 are crushed into small pieces, and as the ground is crushed in this way, it can be seen that the tunnel excavation apparatus 1000 can move forward.

When the ground is excavated using such a tunnel excavation apparatus, there are advantages of increasing worker safety, reducing complaints caused by noise and vibration, and reducing construction costs.

However, when the tunnel excavation apparatus moves forward at a high speed without considering the properties of the ground and the excavation unit is rotated at a high speed, an impact exceeding the capacity of the ground may be applied, causing cracks, etc.

In this way, serious problems may occur when cracks, etc., occur in the ground. For example, when cracks, etc., occur in the ground during the process of excavating the ground for the purpose of storing radioactive waste, problems such as radioactive waste leaking out through the cracks in the ground may occur.

Therefore, it is necessary to control the operation of the tunnel excavation apparatus so that the ground is excavated while considering the properties of the ground so that 'the impact exceeding the acceptable limit is not applied to the ground.

Meanwhile, there may be a method of investigating the properties of the ground to be excavated in advance as a way to consider the properties of the ground when excavating the ground with the tunnel excavation apparatus. However, the method makes it difficult to obtain accurate information on the properties of the ground which change continuously during the excavation process.

Therefore, it is necessary to develop a tunnel excavation apparatus that acquires information on the ground being excavated by the tunnel excavation apparatus in real time and has its operation controlled based on the acquired information on the ground so that the impact exceeding the acceptable limit is not applied to the ground during the excavation process.

DISCLOSURE

Technical Problem

An object of the present disclosure provides a tunnel excavation apparatus to which a spectroscopic analysis method is applied, which can obtain information on excavated ground more accurately and in real time.

Another object of the present disclosure provides a tunnel excavation apparatus to which a spectroscopic analysis method is applied, which can excavate ground without applying an impact that causes cracks in the ground.

Aspects of the present disclosure are not limited to the above-described aspects. That is, other aspects that are not described may be obviously understood by those skilled in the art from the following specification.

Technical Solution

In one general aspect, a tunnel excavation apparatus to which a spectroscopic analysis method is applied includes: a main body; a first driving unit that is connected to the main body and moves the main body forward; an excavation unit that is rotatably installed in front of the main body and contacts the ground to excavate the ground; a second driving unit that is installed on the main body so as to be connected to the excavation unit and rotates the excavation unit; a ground component measurement unit that measures a component of the ground excavated by the excavation unit using a laser induced breakdown spectrometer; and a control unit that controls an operation of the tunnel excavation apparatus to which a spectroscopic analysis method is applied according to the component of the ground.

The control unit may store operation data for operating the first driving unit and the second driving unit according to the components of the ground, and operate the first driving unit and the second driving unit based on the operation data according to the component of the ground measured by the ground component measurement unit.

The ground component measurement unit may suck spoil powder of the ground excavated by the excavation unit, accommodate the spoil powder inside, and then discharge the spoil powder outside, and irradiate a laser to the spoil powder of the ground accommodated inside with the laser induced breakdown spectrometer to measure the component of the ground.

The ground component measurement unit may include: a first suction mechanism that sucks the spoil powder of the ground excavated by the excavation unit; an accommodating mechanism that has a chamber formed to accommodate the spoil powder of the ground sucked by the first suction mechanism and has a transparent window formed on one side through which a laser is transmitted; the laser induced breakdown spectrometer that irradiates the laser to the spoil powder of the ground accommodated in the chamber through the transparent window to measure the component of the ground; and a second suction mechanism that sucks the spoil powder of the ground accommodated in the chamber and discharges the spoil powder from the accommodating mechanism.

The laser induced breakdown spectrometer may include: an irradiation module that irradiates the laser to a predetermined target; and a light receiving module that receives light of plasma generated from the predetermined target by the laser irradiated to the predetermined target, and a distance between the chamber of an outer peripheral edge of the transparent window and the irradiation module may be equal to a focal length of the laser irradiated by the irradiation module.

The excavation unit may include: an excavation unit body that is connected to the second driving unit and rotatably coupled to the main body; and an excavation member that is installed in the excavation unit body to crush the ground when the excavation unit body comes into contact with the ground while rotating.

The excavation member may be composed of a plurality of disc cutters.

Details of other embodiments for solving the problem are included in the description and drawings of the invention.

Advantageous Effects

According to the solution to the problem of the present disclosure described above, since the tunnel excavation apparatus to which a spectroscopic analysis method is applied according to the present disclosure measures properties of excavated ground using a ground component measurement unit configured so that a focal length of laser irradiated by a laser induced breakdown spectrometer is positioned on the ground whose properties are to be measured, it is possible to obtain information on the excavated ground more accurately and in real time.

In addition, since the first driving unit and the second driving unit are controlled to operate based on the information on the ground measured through the ground component measurement unit, it is possible to prevent cracks, etc., from occurring in the ground during the ground excavation process.

DETAILED DESCRIPTION

Figure 1:
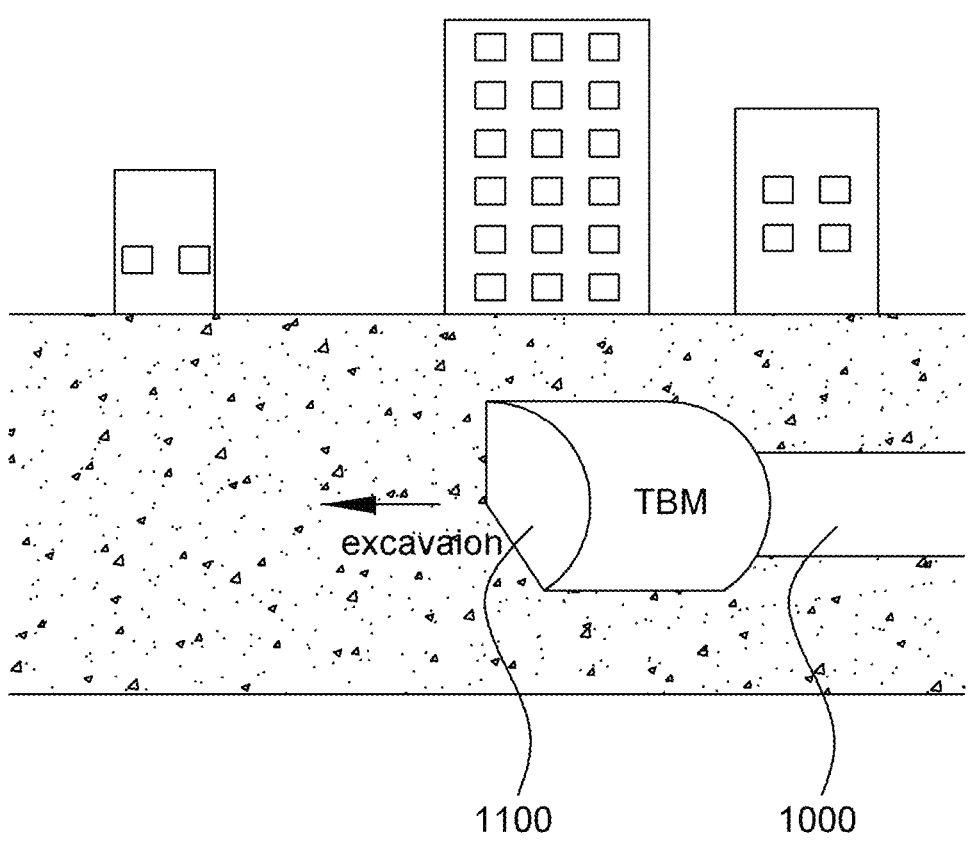
FIG. 1 is a diagram illustrating a concept of tunnel construction using a tunnel excavation apparatus.
Figure 2:
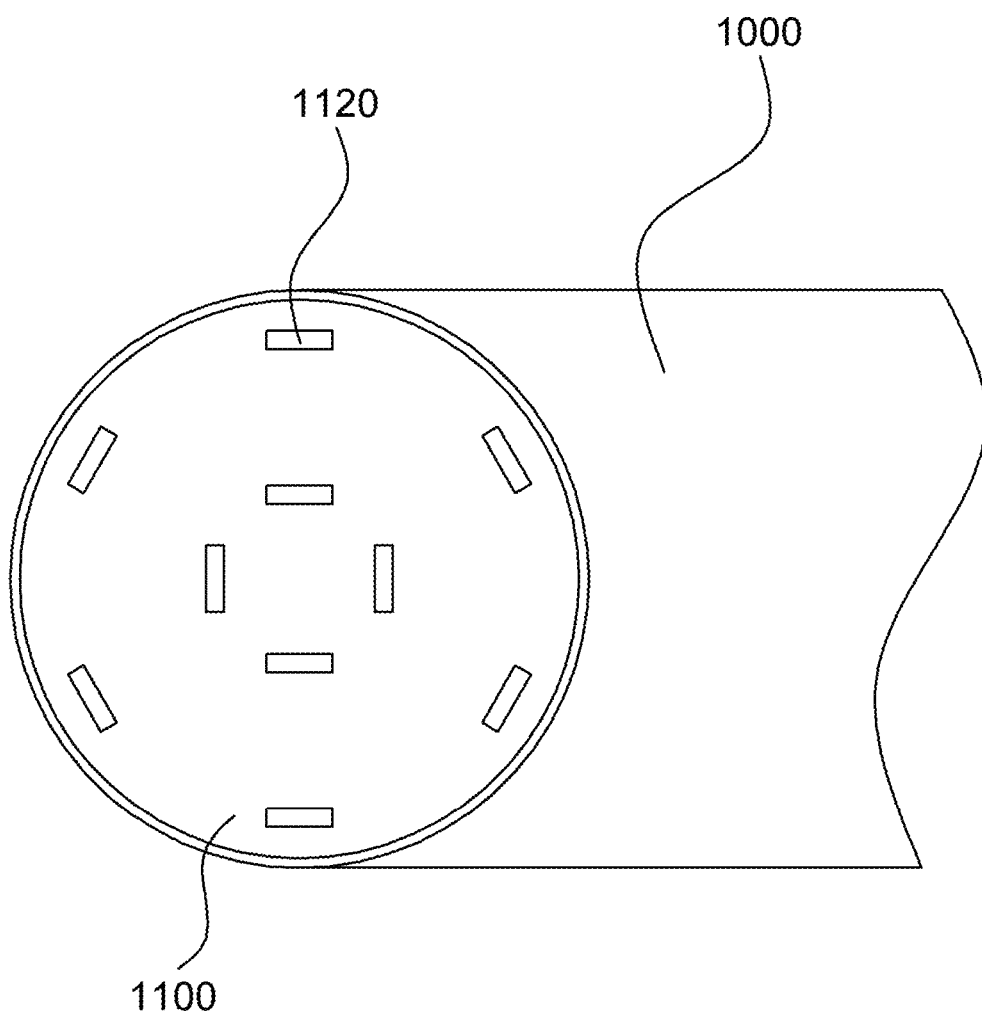
FIG. 2 is a perspective view of an excavation unit of the tunnel excavation apparatus.
Figure 3:
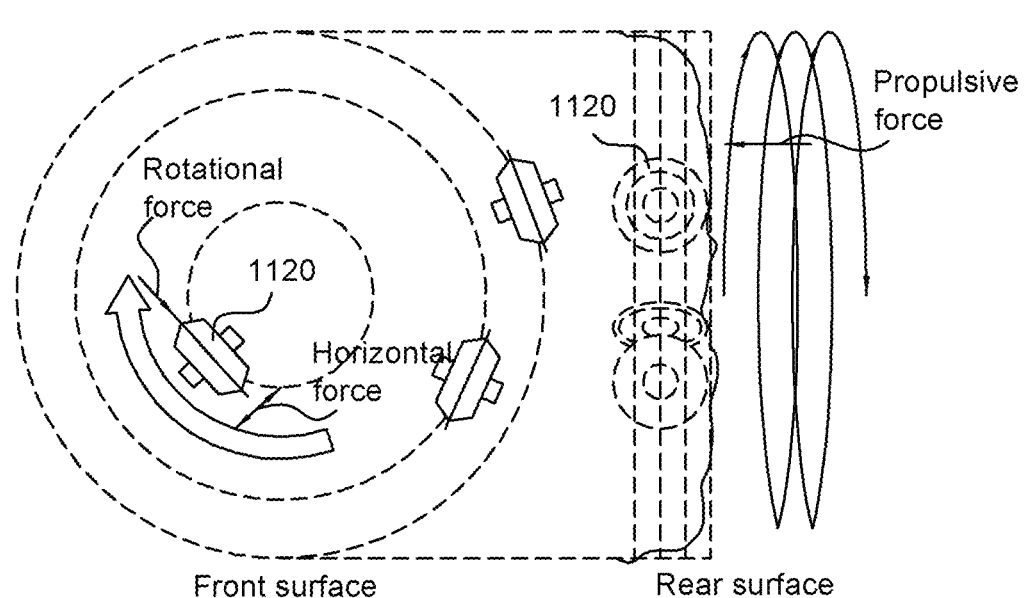
FIG. 3 is a diagram illustrating a concept of an excavation principle of the tunnel excavation apparatus.

Hereinafter, exemplary embodiments of the present disclosure will be described in detail with reference to the accompanying drawings so that those skilled in the art to which the present disclosure pertains may easily practice. However, the present disclosure may be implemented in various different forms, and is not limited to the embodiments described herein. In addition, in the drawings, portions unrelated to the description will be omitted to clearly describe the present disclosure, and similar portions will be denoted by similar reference numerals throughout the specification.

Throughout the present specification, when any one part is referred to as being "connected to" another part, it means that any one part and another part are "directly connected to" each other or are "electrically connected to" each other with still another part interposed therebetween.

Throughout the present specification, when any member is referred to as being positioned "on" other member, it includes not only a case in which any member and another member are in contact with each other, but also a case in which the other member is interposed between any member and another member.

Throughout the present specification, "including" any component will be understood to imply the inclusion of other components rather than the exclusion of other components, unless explicitly described to the contrary. The terms "about," "substantially," and the like used throughout the present specification means figures corresponding to manufacturing and material tolerances specific to the stated meaning and figures close thereto, and are used to prevent unconscionable abusers from unfairly using the disclosure of figures precisely or absolutely described to aid the understanding of the present disclosure. The term "~step" or "~step of" used throughout the present specification of the present disclosure does not mean "~step for."

Hereinafter, embodiments of the present disclosure will be described in detail with reference to the accompanying drawings. However, the present disclosure is not limited to exemplary embodiments herein, but may be implemented in other forms. Same reference numerals denote same constituent elements throughout the specification.

Hereinafter, a configuration of a tunnel excavation apparatus to which a spectroscopic analysis method is applied according to an embodiment of the present disclosure will be described.

Figure 4:
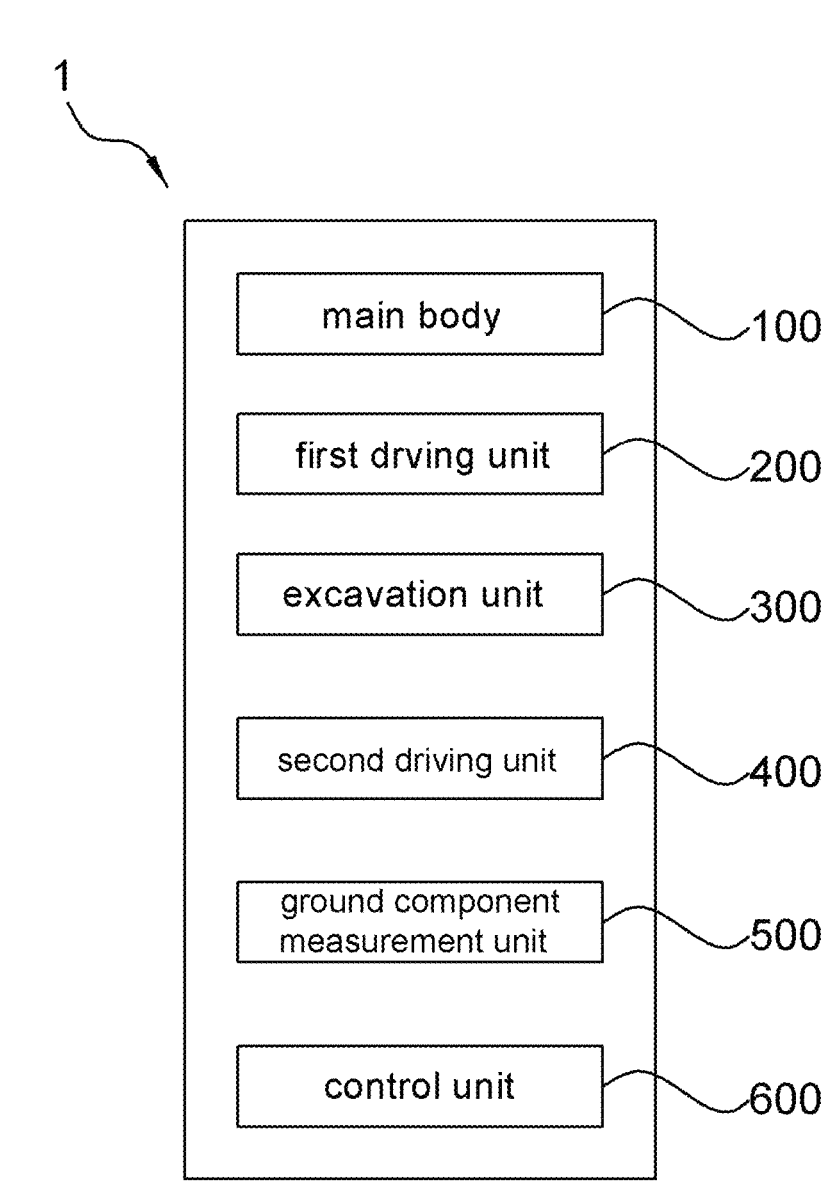
FIG. 4 is a block diagram illustrating a tunnel excavation apparatus to which a spectroscopic analysis method is applied according to an embodiment of the present disclosure.

FIG. 4 is a block diagram illustrating a tunnel excavation apparatus to which a spectroscopic analysis method is applied according to an embodiment of the present disclosure.

Referring to FIG. 4, tunnel excavation apparatus 1 to which a spectroscopic analysis method is applied includes a main body 100, a first driving unit 200, an excavation unit 300, a second driving unit 400, a ground component measurement unit 500, and a control unit 600.

First, the main body 100 will be described.

The main body 100 is formed so that components of tunnel excavation apparatus 1 to which a spectroscopic analysis method is applied may be mounted therein, and may be formed in a shape extending in a longitudinal direction. That is, the main body 100 is provided with components including the first driving unit 200, the excavation unit 300, the second driving unit 400, the ground component measurement unit 500, and the control unit 600, and in addition, may be provided with various equipment necessary for excavation, such as a drilling circulation unit that discharges soil generated when the tunnel excavation apparatus 1 to which a spectroscopic analysis method performs excavation to the outside.

Next, the first driving unit 200 will be described.

The first driving unit 200 may be connected to the main body 100 and perform a function of generating a driving force to move the main body 100 forward. For example, the first driving unit 200 may slide the front of the main body 100 in a front-back direction by a reaction force that is stretched in the longitudinal direction.

The first driving unit 200 may be formed in a structure that it is composed of a conventional hydraulic cylinder controlled by hydraulic pressure, a motor, etc., to move the main body 100 forward.

Next, the excavation unit 300 will be described.

The excavation unit 300 is rotatably installed in front of the main body 100, and may perform the function of excavating the ground by coming into contact with the ground.

Figure 5:
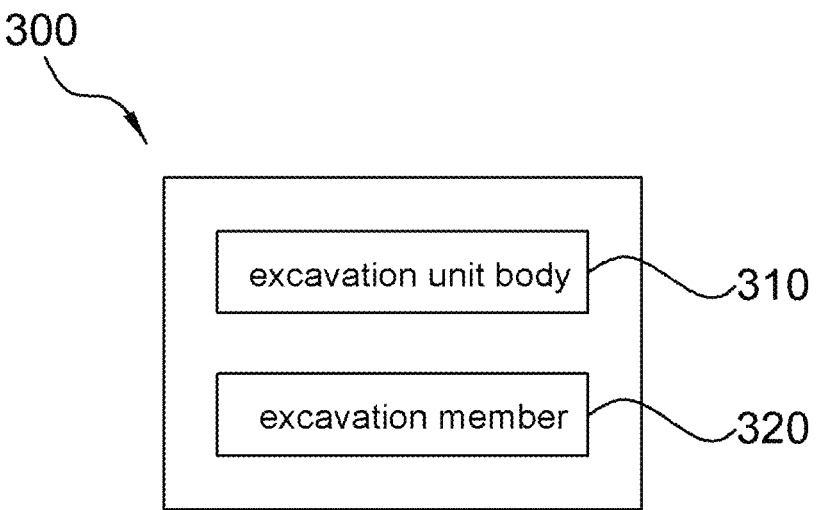
FIG. 5 is a block diagram illustrating the excavation unit.

FIG. 5 is a block diagram illustrating the excavation unit.

Referring to FIG. 5, the excavation unit 300 may include an excavation unit body 310 and an excavation member 320.

The excavation unit body 310 is rotatably coupled to the front of the main body 100, and may be connected to the second driving unit 400 to be described later so as to receive a rotational force from the second driving unit 400 and rotate.

The excavation unit body 310 may be formed in a disk shape, and may continuously change the position of the excavation member 320 to be described later by the rotation operation to improve the excavation efficiency of the tunnel excavation apparatus 1 to which a spectroscopic analysis method is applied.

The excavation member 320 is installed in front of the excavation unit body 310, and may be configured to crush the ground when the excavation unit body 320 comes into contact with the ground while rotating.

For example, the excavation member 320 may be composed of a plurality of disk cutters and installed in front of the excavation unit body 310.

Next, the second driving unit 400 will be described.

The second driving unit 400 is installed in the main body 100, and may be connected to the excavation unit 300 to transmit the rotational force, thereby rotating the excavation unit 300.

For example, the second driving unit 400 may include a motor that is installed inside the main body 100 to generate a rotational force, an output shaft of the motor, and a power transmission member that is connected to the excavation unit body 310 to transmit the rotational force of the motor to the excavation unit body 310.

Next, the ground component measurement unit 500 will be described.

The ground component measurement unit 500 may suck spoil powder of ground excavated by the excavation unit 300, accommodate the spoil powder inside, and then discharge the spoil powder outside. When the excavation unit 300 comes into contact with the ground while rotating, the ground is crushed, and some of the crushed ground floats in the air in the form of powder. The ground component measurement unit 500 may suck the spoil powder of the ground floating in the air in this way, accommodate the spoil powder inside, and then discharge the spoil powder outside.

The ground component measurement unit 500 may measure components of ground by irradiating a laser to the spoil powder of the ground accommodated inside by a laser induced breakdown spectrometer (LIBS).

Figure 6:
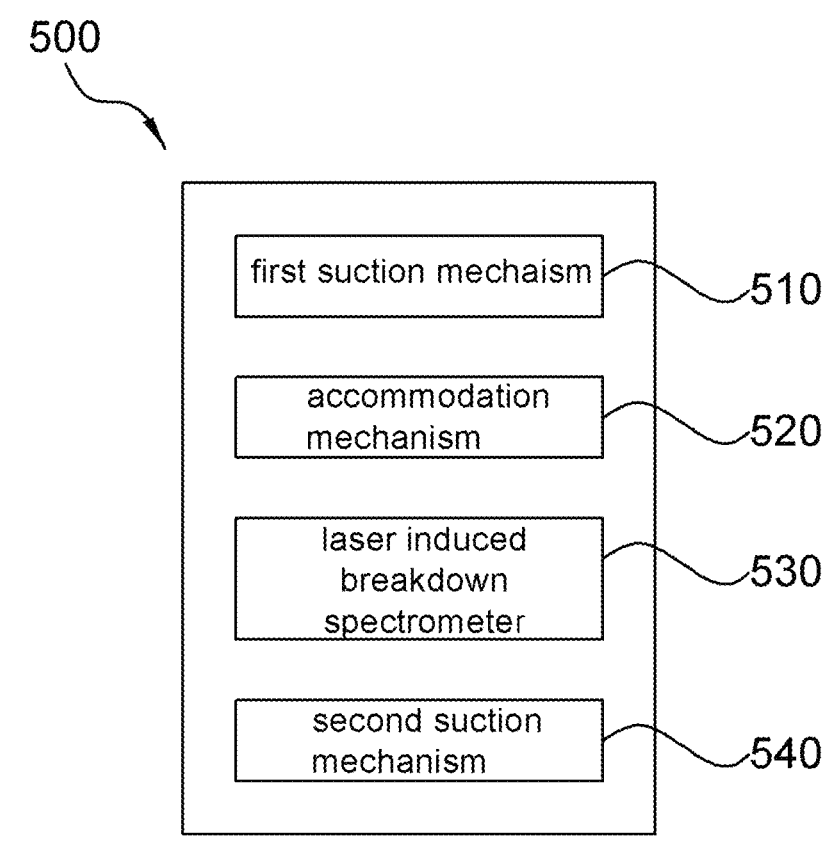
FIG. 6 is a block diagram illustrating a ground component measurement unit.
Figure 7:
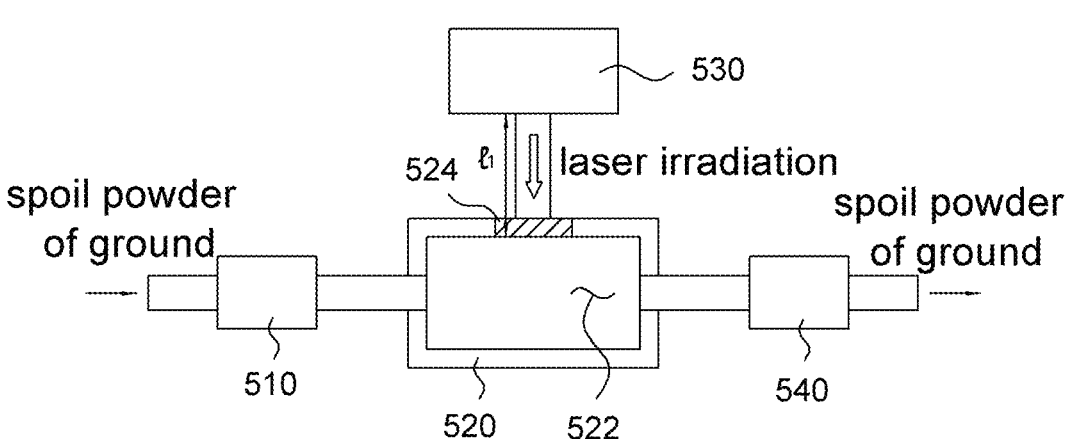
FIG. 7 is a diagram illustrating the ground component measurement unit.

FIG. 6 is a block diagram illustrating the ground component measurement unit, and FIG. 7 is a diagram illustrating the ground component measurement unit.

Specifically, referring to FIGS. 6 and 7, the ground component measurement unit 500 includes a first suction mechanism 510, an accommodating mechanism 520, a laser induced breakdown spectrometer 530, and a second suction mechanism 540.

The first suction mechanism 510 may perform a function of sucking the spoil powder of the ground excavated by the excavation unit 300, and may be configured as the conventional vacuum suction device, etc.

The spoil powder of the ground sucked by the first suction mechanism 510 is transferred to the accommodating mechanism 520 to be described later.

The accommodating mechanism 520 is connected to the first suction mechanism 510, and may perform a function of accommodating the spoil powder of the ground sucked and transferred by the first suction mechanism 510.

A chamber 522 capable of accommodating the spoil powder of the ground may be formed inside the accommodating mechanism 520, and the spoil powder of the ground accommodated inside the chamber 522 may float inside the chamber 522 and be discharged outside the accommodating mechanism 520 by the second suction mechanism 540 to be described later.

In addition, a transparent window 524 through which a laser can transmit may be formed on one side of the accommodating mechanism 520. The transparent window 524 may be formed of a material such as glass so that the laser irradiated from the laser induced breakdown spectrometer 530 to be described later may be transmitted through the transparent window 524 and irradiated to the spoil powder of the ground accommodated inside the chamber 522.

The laser induced breakdown spectrometer 530 may be configured as the conventional device that may analyze components of a sample by irradiating a laser to a sample and receiving light generated from plasma generated from the sample by the irradiated laser, and may perform a function of measuring the components of the ground by irradiating a laser to the spoil powder of the ground accommodated in the chamber 522.

Figure 8:
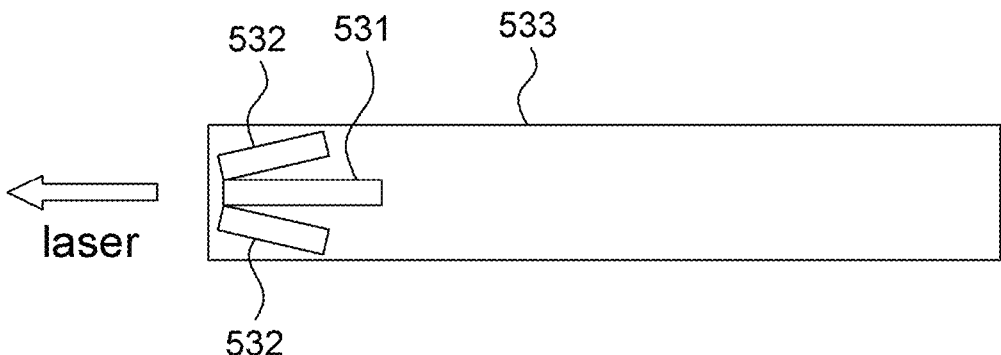
FIG. 8 is a diagram illustrating a laser induced breakdown spectrometer.

FIG. 8 is a diagram illustrating the laser induced breakdown spectrometer.

Referring to FIG. 8, the laser induced breakdown spectrometer 530 includes an irradiation module 531, a light receiving module 532, and a case 533.

The irradiation module 531 may be formed to irradiate a laser to a predetermined target. To this end, the irradiation module 531 may include at least one lens, and a focus of the laser irradiated from the irradiation module 531 may be formed on a focal length determined by at least one lens. When the focus of such laser is formed on a surface of a predetermined target, the largest amount of plasma may be generated from the predetermined target.

When the largest amount of plasma is generated from the predetermined target, the light of the plasma is effectively received by the light receiving module 532 to be described later, so the components of the predetermined target may be analyzed more accurately.

The light receiving module 532 may be formed to receive the light of the plasma generated from the predetermined target by the laser irradiated by the irradiation module 531. To this end, the light receiving module 532 may also be formed to include at least one lens, and the focal length of at least one lens of the light receiving module 532 may be set so that the focus of the image sensed by the light receiving module 532 is formed at a position spaced apart by a predetermined distance from the focus formed by the laser, for example, around the focus formed by the laser.

Therefore, when the focus of the laser irradiated by the irradiation module 531 is positioned on the surface of the sample, the light receiving module 532 may sense an image whose focus is aligned with the plasma generated from the sample. The light receiving module 532 may be arranged around the irradiation module 531 to increase the efficiency of receiving the light of the plasma.

The case 533 may perform a function of accommodating the irradiation module 531 and the light receiving module 532 inside, and may form the exterior of the laser induced breakdown spectrometer 530.

Meanwhile, since the largest amount of plasma is generated from the predetermined target when the focus of the laser irradiated from the irradiation module 531 is formed on the surface of the predetermined target, it is preferable that the focus of the laser irradiated from the irradiation module 531 is formed on the surface of the spoil powder of the ground in order to measure the components of the ground more accurately.

In addition, in order for the focus of the laser irradiated from the irradiation module 531 to be formed on the surface of the spoil powder of the ground, the focus of the laser irradiated from the irradiation module 531 needs to be formed in the chamber 522 of the outer peripheral edge of the transparent window 524.

That is, since the spoil powder of the ground accommodated inside the chamber 522 is distributed to all spaces inside the chamber 522 while floating inside the chamber 522, when the focus of the laser irradiated from the irradiation module 531 is formed in the chamber 522 of the outer peripheral edge of the transparent window 524, the focus of the laser irradiated from the irradiation module 531 may be formed on the surface of the spoil powder of the ground.

Therefore, as illustrated in FIG. 7, when a distance 11 between the chamber 522 of the outer peripheral edge of the transparent window 524 and the irradiation module 531 of the laser induced breakdown spectrometer 530 is made equal to the focal length of the laser irradiated by the irradiation module 531, the focus of the laser irradiated from the irradiation module 531 is formed in the chamber 522 of the outer peripheral edge of the transparent window 524, so that the components of the ground may be measured more accurately. The second suction mechanism 540 may perform the function of sucking the spoil powder of the ground accommodated in the chamber 522 of the accommodating mechanism 520 and discharging the spoil powder from the accommodating mechanism 520, and may be configured as the conventional vacuum suction device, etc.

The spoil powder of the ground sucked by the second suction mechanism 540 may be discharged outside the ground component measurement unit 500.

Next, the control unit 600 will be described.

The control unit 600 may control the operation of the components of the tunnel excavation apparatus 1 to which a spectroscopic analysis method is applied so that the operation of the tunnel excavation apparatus 1 to which a spectroscopic analysis method is applied is controlled according to the components of the ground excavated by the tunnel excavation apparatus 1 to which a spectroscopic analysis method is applied.

In general, the harder the ground excavated by the tunnel excavation apparatus 1 to which a spectroscopic analysis method is applied, the slower the excavation speed, so it is possible to minimize the impact on the ground.

In other words, the excavation speed should be adjusted differently according to the properties of the ground excavated by the tunnel excavation apparatus 1 to which a spectroscopic analysis method is applied, thereby preventing cracks, etc., from occurring in the ground during the ground excavation process.

To solve this problem, the control unit 600 may store operation data for operating the first driving unit 200 and the second driving unit 400 according to the components of the ground, receive the operation data according to the components of the ground measured by the ground component measurement unit 500, and operate the first driving unit 200 and the second driving unit 400 based on the received operation data.

The operation data includes information for operating the first driving unit 200 and the second driving unit 400 according to the components of the ground so that the advance speed of the main body 100 and the rotation speed of the excavation unit 300 vary according to the components of the ground with different strength.

For example, when the ground measured by the ground component measurement unit 500 has a relatively high strength, the operation data may include information for the first driving unit 200 to forward move the main body 100 relatively slowly and the second driving unit 400 to rotate the excavation unit 300 relatively slowly.

On the other hand, when the ground measured by the ground component measurement unit 500 has a relatively low strength, the operation data may include information for the first driving unit 200 to forward move the main body 100 relatively quickly and the second driving unit 400 to rotate the excavation unit 300 relatively quickly.

Hereinafter, the operation and effect of the tunnel excavation apparatus to which a spectroscopic analysis method is applied of the present disclosure will be described.

The ground is excavated using the tunnel excavation apparatus 1 to which a spectroscopic analysis method is applied while measuring the components of the ground by the ground component measurement unit 500.

In this case, the ground component measurement unit 500 may suck the spoil powder of the ground to measure the components of the ground using the laser induced breakdown spectrometer 530, and the focus of the laser irradiated from the laser induced breakdown spectrometer 530 is formed on the surface of the spoil powder of the ground, so the components of the ground may be measured more accurately in real time.

When the information on the components of the ground measured by the ground component measurement unit 500 is transmitted to the control unit 600, the control unit 600 controls the operation of the first driving unit 200 and the second driving unit 400 so that the advance speed of the main body 100 and the rotation speed of the excavation unit 300 vary according to the measured components of the ground.

Specifically, when the ground strength measured by the ground component measurement unit 500 is relatively large, the control unit 600 may control the operation of the first driving unit 200 and the second driving unit 400 so that the tunnel excavation apparatus 1 to which a spectroscopic analysis method is applied excavates the ground at a slow speed, and when the ground strength measured by the ground component measurement unit 500 is relatively small, may control the operation of the first driving unit 200 and the second driving unit 400 so that the tunnel excavation apparatus 1 to which a spectroscopic analysis method is applied excavates the ground at a fast speed.

Accordingly, since the tunnel excavation apparatus to which a spectroscopic analysis method is applied according to the present disclosure measures properties of excavated ground using a ground component measurement unit configured so that a focal length of laser irradiated by a laser induced breakdown spectrometer is positioned on the ground whose properties are to be measured, it is possible to obtain information on the excavated ground more accurately and in real time.

In addition, since the first driving unit and the second driving unit are controlled to operate based on the information on the ground measured through the ground component measurement unit, it is possible to prevent cracks, etc., from occurring in the ground during the ground excavation process.

The description of the present disclosure provided above is illustrative, and it is to be understood by those skilled in the art that various modifications and alterations may be made without departing from the spirit or essential feature of the present disclosure. Therefore, it is to be understood that the exemplary embodiments described above are illustrative rather than being restrictive in all aspects. For example, respective components described as a single form may be implemented in a distributed manner, and similarly, components described as being distributed may also be implemented in a combined form.

It is to be understood that the scope of the present disclosure will be defined by the claims rather than the above-described description and all modifications and alternations derived from the claims and their equivalents are included in the scope of the present disclosure.

The invention claimed is:

1. A tunnel excavation apparatus to which a spectroscopic analysis method is applied, comprising:
   a main body;
   a first driving unit that is connected to the main body and moves the main body forward;
   an excavation unit that is rotatably installed in front of the main body and contacts the ground to excavate the ground;
   a second driving unit that is installed on the main body so as to be connected to the excavation unit and rotates the excavation unit;

a ground component measurement unit that measures a component of the ground excavated by the excavation unit using a laser induced breakdown spectrometer; and
   a control unit that controls an operation of the tunnel excavation apparatus to which a spectroscopic analysis method is applied according to the component of a ground, and wherein the ground component measurement unit sucks spoil powder of the ground excavated by the excavation unit, accommodates the spoil powder inside, and then discharges the spoil powder outside, and
   irradiates a laser to the spoil powder of the ground accommodated inside with the laser induced breakdown spectrometer to measure the component of the ground, and wherein the ground component measurement unit includes a first suction mechanism that sucks the spoil powder of the ground excavated by the excavation unit, an accommodating mechanism that has a chamber formed to accommodate the spoil powder of the ground sucked by the first suction mechanism and has a transparent window formed on one side through which a laser is transmitted, the laser induced breakdown spectrometer that irradiates the laser to the spoil powder of the ground accommodated in the chamber through the transparent window to measure the component of the ground, and a second suction mechanism that sucks the spoil powder of the ground accommodated in the chamber and discharges the spoil powder from the accommodating mechanism.

2. The tunnel excavation apparatus of claim 1, wherein the control unit stores operation data for operating the first driving unit and the second driving unit according to the component of the ground, and operates the first driving unit and the second driving unit based on the operation data according to the component of the ground measured by the ground component measurement unit.

3. The tunnel excavation apparatus of claim 2, wherein the laser induced breakdown spectrometer includes:
   an irradiation module that irradiates the laser to a predetermined target; and
   a light receiving module that receives light of plasma generated from the predetermined target by the laser irradiated to the predetermined target, and
   a distance between the chamber of an outer peripheral edge of the transparent window and the irradiation module is equal to a focal length of the laser irradiated by the irradiation module.

4. The tunnel excavation apparatus of claim 3, wherein the excavation unit includes:
   an excavation unit body that is connected to the second driving unit and rotatably coupled to the main body; and
   an excavation member that is installed in the excavation unit body to crush the ground when the excavation unit body comes into contact with the ground while rotating.

5. The tunnel excavation apparatus of claim 4, wherein the excavation member is composed of a plurality of disc cutters.

* * * * *